United States Patent
Fogg (10) Patent No.: US 9,901,259 B2
(45) Date of Patent: Feb. 27, 2018

(54) SYSTEM FOR GENERATING CARDIAC AND OTHER ELECTRIC WAVEFORMS

(71) Applicant: Harold T. Fogg, Aurora, CO (US)

(72) Inventor: Harold T. Fogg, Aurora, CO (US)

( * ) Notice: Subject to any disclaimer, the term of this patent is extended or adjusted under 35 U.S.C. 154(b) by 117 days.

(21) Appl. No.: 15/013,873

(22) Filed: Feb. 2, 2016

(65) Prior Publication Data
US 2016/0220138 A1 Aug. 4, 2016

Related U.S. Application Data

(60) Provisional application No. 62/111,500, filed on Feb. 3, 2015.

(51) Int. Cl.
| | |
|---|---|
| *A61B 5/02* | (2006.01) |
| *A61B 5/0402* | (2006.01) |
| *A61N 1/37* | (2006.01) |
| *G06F 19/00* | (2018.01) |

(52) U.S. Cl.
CPC ............ *A61B 5/02* (2013.01); *A61B 5/02028* (2013.01); *A61B 5/04021* (2013.01); *A61N 1/3706* (2013.01); *G06F 19/3437* (2013.01)

(58) Field of Classification Search
CPC ............ A61B 5/04021; A61B 5/02028; A61N 1/3706; G06F 19/3437
See application file for complete search history.

(56) References Cited

U.S. PATENT DOCUMENTS

| | | | | |
|---|---|---|---|---|
| 4,290,430 A | * | 9/1981 | Bihn .................... | A61N 1/3706 607/27 |
| 6,049,730 A | * | 4/2000 | Kristbjarnarson . | A61B 5/04011 600/509 |
| 2009/0030292 A1 | * | 1/2009 | Bartnik .............. | A61B 5/02028 600/301 |
| 2016/0135704 A1 | * | 5/2016 | Zhang ................ | A61B 5/04012 600/515 |

* cited by examiner

*Primary Examiner* — Ajay Ojha
(74) *Attorney, Agent, or Firm* — Shifrin Patent Law; Dan Shifrin (57) ABSTRACT

A system is provided for generating electrical signals. The system comprises: an input configured to receive first values, the first values representing coordinates of a plurality of break points of a heart beat waveform, and further configured to output programming signals; a communication port configured to receive the programming signals from the control panel; a memory configured to store instructions and predetermined values; a processor configured to process the programming signals and predetermined values according to the instructions stored in the memory; and an output port configured to make the processed signals available to a system under test.

23 Claims, 8 Drawing Sheets

| | $M_1$ | $M_2$ | $M_3$ | $M_4$ | $M_5$ | $M_6$ | $M_7$ | $M_8$ | $M_9$ | $M_{10}$ | $M_{11}$ | $M_{12}$ | $M_{13}$ | $M_{14}$ | $M_{15}$ | $M_{16}$ | $M_{17}$ | $M_{18}$ |
|---|---|---|---|---|---|---|---|---|---|---|---|---|---|---|---|---|---|---|
| | 0 | $P_1$ | $P_2$ | $P_3$ | $Q_1$ | $Q_2$ | $Q_3, R_1$ | $R_2$ | $R_3, S_1$ | $S_2$ | $S_3$ | $T_1$ | $T_2$ | $T_3$ | $U_1$ | $U_2$ | $U_3$ | |
| $M_1$ — 0 | 0 | 0 | - | - | - | - | - | - | - | - | - | - | - | - | - | - | - | - |
| $M_2$ — $P_1$ | - | 0 | $P_2-P_1$ | $P_3-P_1$ | - | - | - | - | - | - | - | $T_1-P_1$ | - | - | - | - | - | - |
| $M_3$ — $P_2$ | - | - | 0 | $P_3-P_2$ | - | - | - | - | - | - | - | - | - | - | - | - | - | - |
| $M_4$ — $P_3$ | - | - | - | 0 | - | - | $Q_3-P_3$ | - | - | - | - | - | - | - | $U_1-P_3$ | - | - | - |
| $M_5$ — $Q_1$ | - | - | - | - | 0 | - | - | - | - | - | $Q_1-S_3$ | $T_1-Q_1$ | - | - | - | - | - | - |
| $M_6$ — $Q_2$ | - | - | - | - | - | 0 | - | - | - | - | - | - | - | - | - | - | - | - |
| $M_7$ — $Q_3, R_1$ | - | - | - | - | - | - | 0 | - | $R_3-R_1$ | - | - | - | - | - | - | - | - | - |
| $M_8$ — $R_2$ | - | - | - | - | - | - | - | 0 | - | - | - | $T_1-R_2$ | - | - | - | - | - | - |
| $M_9$ — $R_3, S_1$ | - | - | - | - | - | - | - | - | 0 | - | - | - | - | - | - | - | - | - |
| $M_{10}$ — $S_2$ | - | - | - | - | - | - | - | - | - | 0 | - | - | - | - | - | - | - | - |
| $M_{11}$ — $S_3$ | - | - | - | - | - | - | - | - | - | - | 0 | $T_1-S_3$ | - | - | - | - | - | - |
| $M_{12}$ — $T_1$ | - | - | - | - | - | - | - | - | - | - | - | 0 | - | $T_3-T_1$ | - | - | - | - |
| $M_{13}$ — $T_2$ | - | - | - | - | - | - | - | - | - | - | - | - | 0 | - | - | - | - | - |
| $M_{14}$ — $T_3$ | - | - | - | - | - | - | - | - | - | - | - | - | - | 0 | - | - | - | - |
| $M_{15}$ — $U_1$ | - | - | - | - | - | - | - | - | - | - | - | - | - | - | 0 | - | $U_1-U_3$ | - |
| $M_{16}$ — $U_2$ | - | - | - | - | - | - | - | - | - | - | - | - | - | - | - | 0 | - | - |
| $M_{17}$ — $U_3$ | - | - | - | - | - | - | - | - | - | - | - | - | - | - | - | - | 0 | - |
| $M_{18}$ | - | - | - | - | - | - | - | - | - | - | - | - | - | - | - | - | - | 0 |

FIG. 5

| | X-coordinate |
|---|---|
| M$_1$ | 0 |
| M$_2$ | P$_1$ |
| M$_3$ | P$_2$ |
| M$_4$ | P$_3$ |
| M$_5$ | Q$_1$ |
| M$_6$ | Q$_2$ |
| M$_7$ | Q$_3$, R$_1$ |
| M$_8$ | R$_2$ |
| M$_9$ | R$_3$, S$_1$ |
| M$_{10}$ | S$_2$ |
| M$_{11}$ | S$_3$ |
| M$_{12}$ | T$_1$ |
| M$_{13}$ | T$_2$ |
| M$_{14}$ | T$_3$ |
| M$_{15}$ | U$_1$ |
| M$_{16}$ | U$_2$ |
| M$_{17}$ | U$_3$ |
| M$_{18}$ | |

FIG. 6

| | Amplitude |
|---|---|
| M$_1$ | 0 |
| M$_2$ | P$_1$ |
| M$_3$ | P$_2$ |
| M$_4$ | P$_3$ |
| M$_5$ | Q$_1$ |
| M$_6$ | Q$_2$ |
| M$_7$ | Q$_3$ |
| M$_8$ | R$_2$ |
| M$_9$ | R$_3$ |
| M$_{10}$ | S$_2$ |
| M$_{11}$ | S$_3$ |
| M$_{12}$ | T$_1$ |
| M$_{13}$ | T$_2$ |
| M$_{14}$ | T$_3$ |
| M$_{15}$ | U$_1$ |
| M$_{16}$ | U$_2$ |
| M$_{17}$ | U$_3$ |
| M$_{18}$ | 0 |

FIG. 7

| | Interpolation Method |
|---|---|
| M$_1$ | 0 |
| M$_2$ | P$_1$ |
| M$_3$ | P$_2$ |
| M$_4$ | P$_3$ |
| M$_5$ | Q$_1$ |
| M$_6$ | Q$_2$ |
| M$_7$ | Q$_3$, R$_1$ |
| M$_8$ | R$_2$ |
| M$_9$ | R$_3$, S$_1$ |
| M$_{10}$ | S$_2$ |
| M$_{11}$ | S$_3$ |
| M$_{12}$ | T$_1$ |
| M$_{13}$ | T$_2$ |
| M$_{14}$ | T$_3$ |
| M$_{15}$ | U$_1$ |
| M$_{16}$ | U$_2$ |
| M$_{17}$ | U$_3$ |
| M$_{18}$ | |

SYSTEM FOR GENERATING CARDIAC AND OTHER ELECTRIC WAVEFORMS

RELATED APPLICATION DATA

The present application is related to and claims the benefit of commonly-assigned and U.S. Provisional Application Ser. No. 62/111,500, entitled SYSTEM FOR GENERATING CARDIAC WAVEFORMS and filed on Feb. 3, 2015, which application is incorporated herein by reference in its entirety. The present invention is also related to commonly-assigned and U.S. patent application Ser. No. 13/625,978, entitled SYSTEM AND METHOD FOR PROVIDING PRODUCTS AND LOCATIONS and filed on Sep. 25, 2012; Ser. No. 14/708,226, entitled SYSTEM AND METHOD FOR SEARCHING, WRITING, EDITING, AND PUBLISHING WAVEFORM SHAPE INFORMATION and filed on May 9, 2015; and 14/940,356, entitled PHYSIOLOGICAL ELECTRICAL SIGNAL SIMULATOR and filed on Nov. 13, 2015, which applications are incorporated by reference in their entireties.

TECHNICAL FIELD

The present invention relates generally to waveform generators and, in particular, to an apparatus and method for stimulating biological activity and simulating electrical signals, including biological process signals such as ECG signals.

BACKGROUND ART

Electrocardiograph (ECG) monitors are important, and non-invasive, diagnostic medical tools. An ECG waveform is a representation of some of the electrical activity produced by a beating heart during a period of time. Two or more electrodes are placed at various location on a patient's skin and connected to an ECG monitor. Electrical signals are generated in the heart. The signals are detected on the skin by the electrodes and received by the ECG monitor. The machine amplifies and processes the signals and converts them into a representation of the heart's activity, which may be analyzed and displayed as traces on a screen, printed onto paper, or both.

Figure 1:
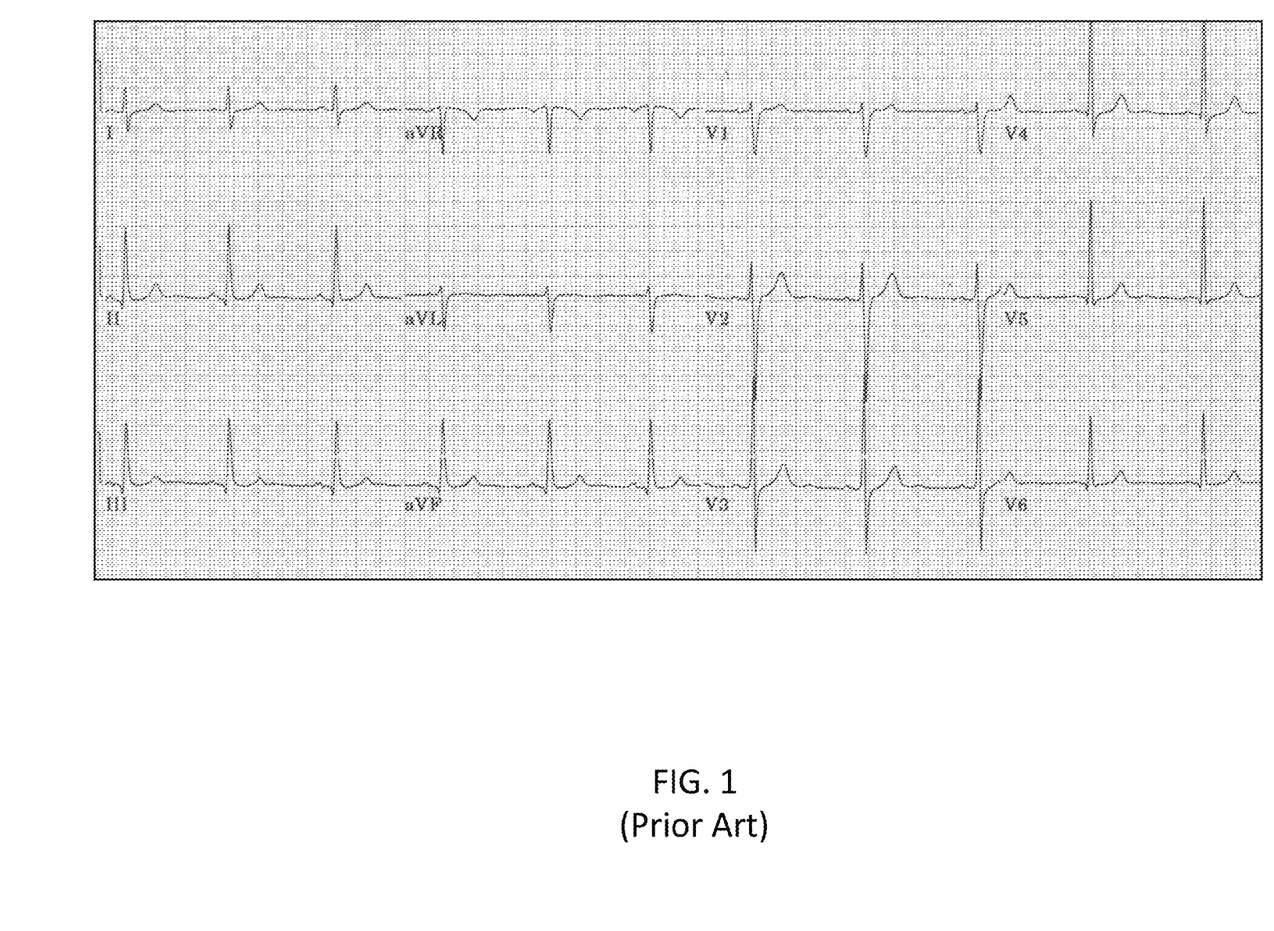
FIG. 1 is a prior art example of a strip chart of electrical signals from a 12-lead ECG monitor connected to a patient with a normal heart.
Figure 2:
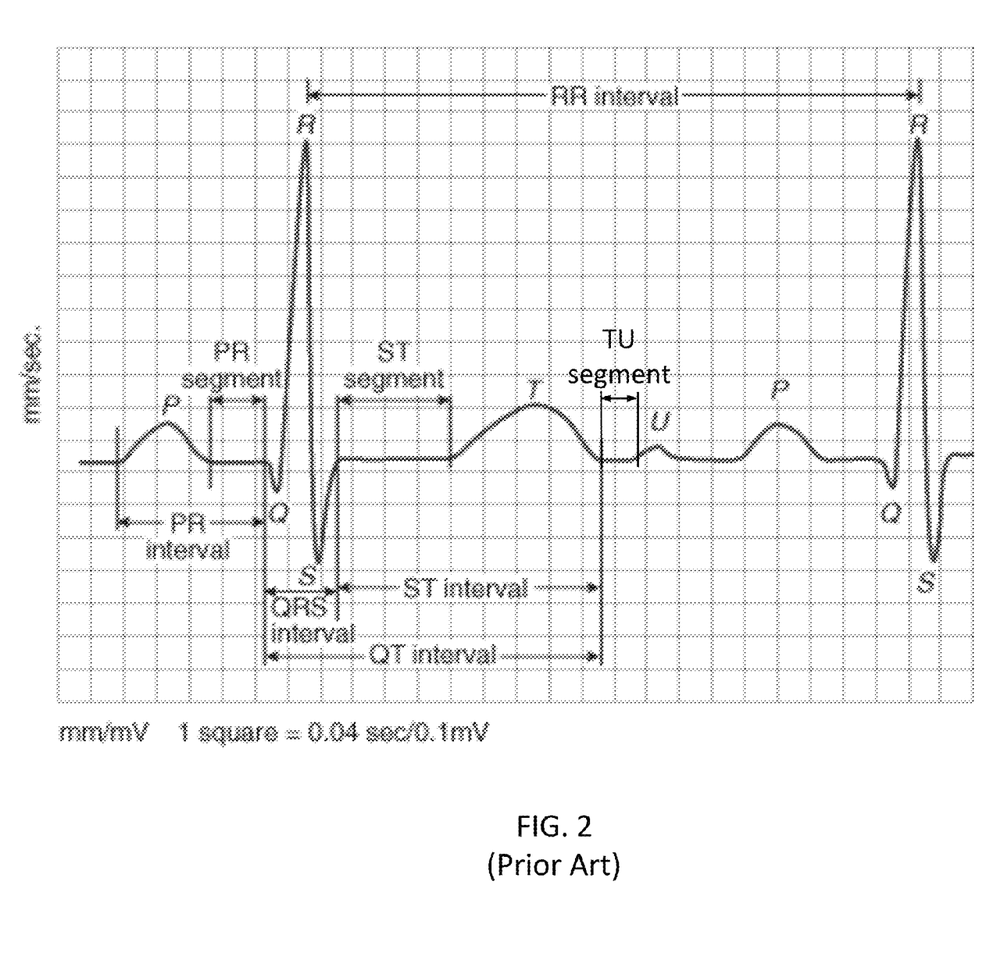

It is not the intent of this discussion to provide a detailed explanation of cardiology and the analysis of ECG traces. However, a general summary is useful for background purposes. FIG. 1 is an example of a strip chart of electrical signals from a 12-lead ECG monitor connected to a patient with a normal heart. FIG. 2 identifies individual waves, intervals, and segments. While there may be some confusion or ambiguity about the labeling of different "sections" of an ECG wave, for purposes of this application an "interval" contains one or more individual wave and a "segment" connects the end of one individual wave with the beginning of the next wave. Beginning from the left side of the chart in FIG. 2, the individual waves are: the P wave, the Q wave, the R wave, the S wave, the T wave, and the U wave (which may be overlapped and hidden by the T wave and the next P wave).

Beginning again from the left side of the chart in FIG. 2, the intervals are:
a. the PR interval, from the start of the P wave to the beginning of the QRS interval;
b. the PQ interval, which if used, is the same as the PR interval when the Q wave is present;
c. the QRS interval (also known as the QRS complex), which extends from the beginning of the Q wave to the end of the S wave;
d. the ST interval, extends from the end of the S wave to the beginning of the T wave; and
e. the QT interval, is measured from the beginning of the QRS interval to the end of the T wave; and
f. the RR interval, extends from the peak of one R wave of one beat to the peak of the next R wave of the next beat.

The segments are:
a. PR segment, extends from the end of the P wave to the beginning of the Q wave;
b. ST segment, extends from the end of the S wave to the beginning of the T wave; and
c. TU segment, extends from the end of the T wave to the beginning of the U wave.

From the scale of the plot of FIG. 2, TABLE I may be populated with the approximate duration of approximate time, in milliseconds, associated with some of the waves, segments, and intervals.

TABLE I

| Name | Duration in milliseconds (approximate) |
| --- | --- |
| Waves | |
| P | 100 |
| Q | 20 |
| R | 40 |
| S | 40 |
| T | 180 |
| U | 40 |
| Segments | |
| PR | 60 |
| ST | 140 |
| TU | 40 |
| Intervals | |
| PR/PQ | 180 |
| QRS | 80 |
| ST | 320 |
| QT | 410 |
| RR | 750 |

Figure 3:
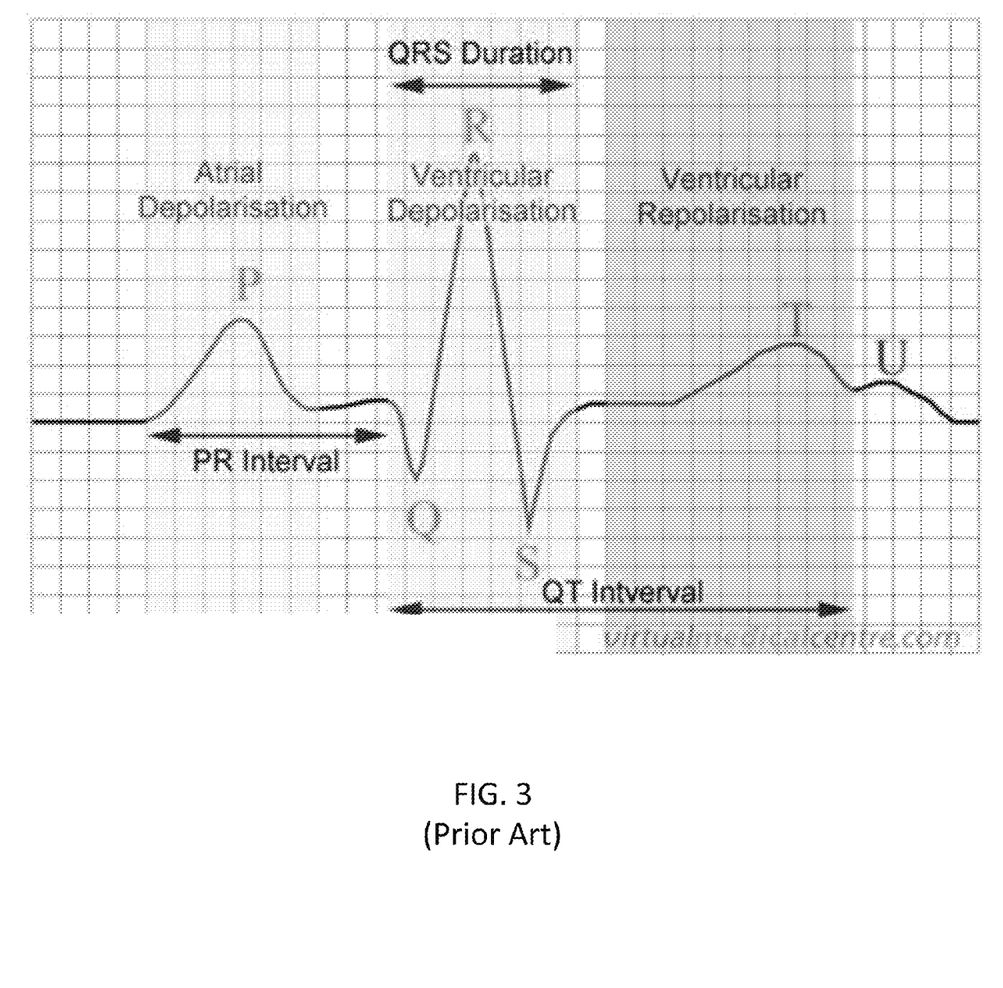
FIG. 3 is a prior art identification of the activity of the heart muscles during each phase of a beat (source: http://paramedicine101.blogspot.com/2009/09/electrocardiogram-part-iv.html)

FIG. 3 identifies the activity of the heart muscles during each of three major phases of a beat:
a. the P wave represents atrial depolarization;
b. the QRS interval represents ventricular depolarization; and
c. the T wave represents ventricular repolarization.

The wave representing atrial repolarization typically occurs between the end of the P wave and the beginning of the T wave, but is typically hidden by ventricular activity.

SUMMARY OF THE INVENTION

The present invention provide systems and methods that allows a user to create an electrical signal, such as an ECG wave form, by defining a series of individual waves, intervals, and segments. The created wave form may then be input to a system under test, such as an ECG monitor whose output may be compared to the input.

The present invention provides a system for generating simulated ECG electrical signals. The apparatus comprises: an input configured to receive first values, the first values representing coordinates for a plurality of break points, and further configured to output programming signals; a communication port configured to receive the programming signals from the control panel; a memory configured to store instructions and predetermined values; a processor configured to process the programming signals and predetermined values according to the instructions stored in the memory; and an output port configured to make the processed signals available to a system under test.

The present invention also provides a method of generating simulated ECG electrical signals. The method comprises displaying a matrix for user input. The matrix comprises: a first row in which a plurality of break points is labeled, the break points identifying the beginning and end of ECG Q, R, S, T, and U waves and a point between the beginning and end of each wave; a first column in which the plurality of break points is listed; a second column configured to receive user input of an amplitude value of each break point on a y-axis; a third column configured to receive user input of a time value of each break point on an x-axis; and a plurality of cells in a remaining portion of the matrix configured to receive user input of a time differential between two adjacent break points. The method further comprises: providing a user with a selection of interpolation methods to define a connection path from one break point to a next break point; as values for each break point are accepted by the user, displaying the break point on a chart as a portion of a heart beat waveform, including the connection path from each break point to the next break point; after all values for the break points have been entered by the user, converting the entered values into a analog signal representing the heart beat waveform; and providing the analog signal to an input of an ECG monitor whereby the ECG monitor displays the heart beat waveform.

The present invention further provides a system for generating simulated ECG electrical signals. The apparatus comprises: an input configured to receive first values, the first values representing coordinates for a plurality of break points of a heart beat waveform, and further configured to output programming signals; a communication port configured to receive the programming signals from the control panel; a memory configured to store instructions and predetermined values; a processor configured to process the programming signals and predetermined values according to the instructions stored in the memory; and an output port configured to make the processed signals available to a system under test.

The present invention also provides a method of generating electrical signals. The method comprises: providing a matrix wherein each cell in the matrix is identified by the intersection of a row and a column; labeling each row and each column for identifying a break point representing a fiducial point; providing for each cell contents comprising the time difference between the fiducial points that identify the cell; providing for each break point a method to define a connection path from the break point to a next break point; converting the contents of the matrix into an analog signal representing the generated electric signal; and outputting the analog signal for graphical display of the generated electric signal.

BRIEF DESCRIPTION OF THE DRAWINGS

FIG. 2 is a prior art identification of the individual waves, intervals and segments that combine to form an ECG wave (source:

http://www.merckmanuals.com/professional/cardiovascular_disorders/cardiovascular_tests_a ndprocedures/electrocardiography_ecg.html);

DETAILED DESCRIPTION OF THE PREFERRED EMBODIMENT

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention. While much of the description and the accompanying figures refer to ECG monitors and ECG waveforms, embodiments of the present invention may also generate other electrical signals for use with other signal monitors.

Relative to the normal shapes and sizes of waves, intervals, and segments, any that are abnormal, absent, varying, long, short, tall, elevated, depressed, flattened, inverted, or prominent may be indicative of various problems.

Embodiments of the present invention provide a system and method for simulating ECG and other electrical signals that are defined by user-selected parameters. The present invention is useful for training medical professionals, for testing monitors, and for evaluating algorithms/diagnostic tools.

Figure 4:
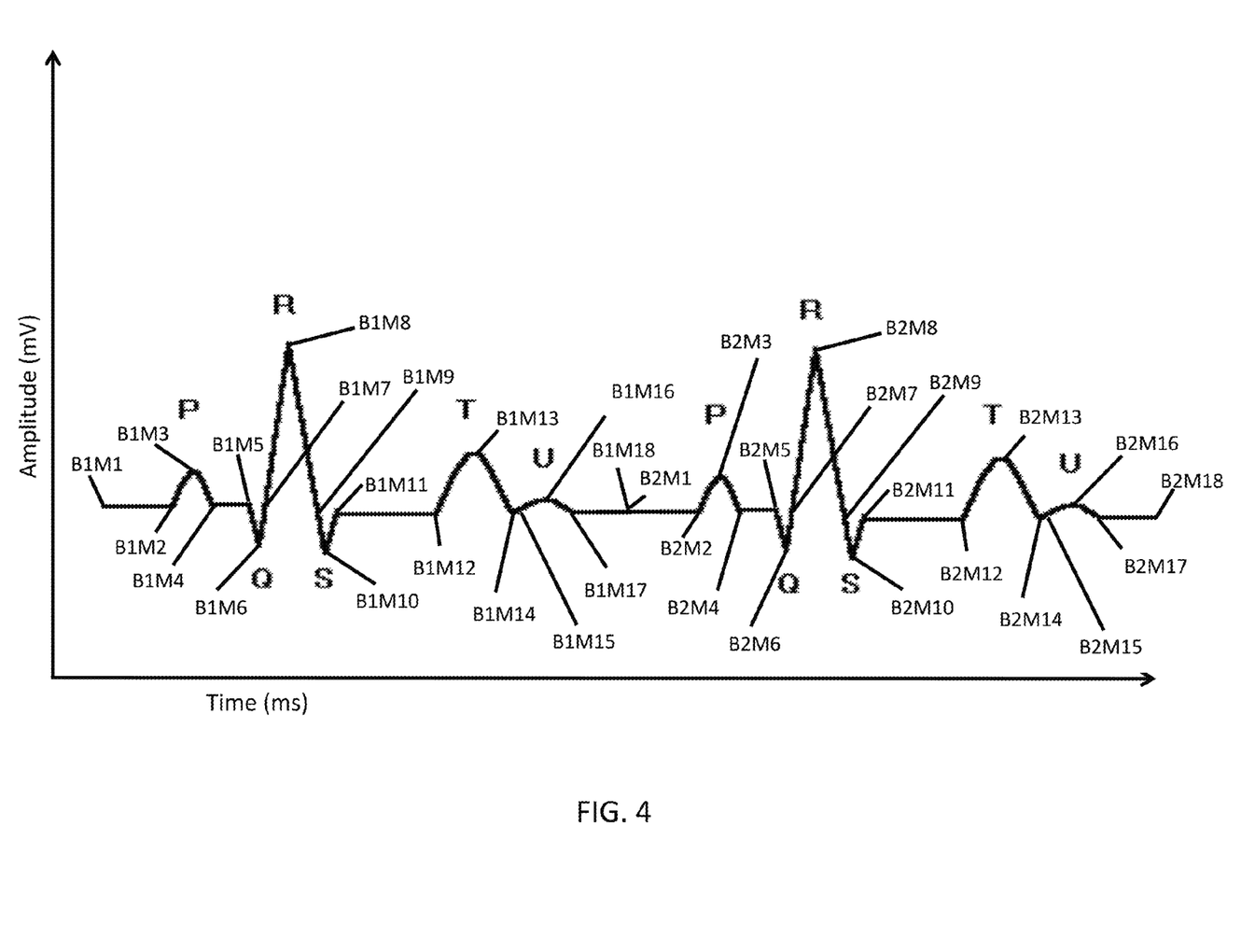
FIG. 4 illustrates an exemplary ECG waveform with transition break points identified.

FIG. 4 illustrates an exemplary ECG waveform showing two beats $B_1$ and $B_2$ with break points $B_1M_1$-$B_1M_{15}$ and $B_2M_1$-$B_2M_{15}$, respectively. The break points $M_1$-$M_{18}$ identify fiducial or transition points of one complete cycle of an ECG waveform. (Any wave, interval, or segment may be referred to generically herein as a "section.") TABLE II provides an identification of the break points as used in this description.

TABLE II

| Break Point | Identifier |
|---|---|
| $M_1$ | Beginning of beat |
| $M_2$ | Beginning of P wave ($P_1$) |
| $M_3$ | Peak of P wave ($P_2$) |
| $M_4$ | End of P wave ($P_3$) |
| $M_5$ | Beginning of Q wave ($Q_1$) |
| $M_6$ | Low point of Q wave ($Q_2$) |
| $M_7$ | End of Q wave ($Q_3$); beginning of R wave ($R_1$) |
| $M_8$ | Peak of R wave ($R_2$) |
| $M_9$ | End of R wave ($R_3$); beginning of S wave ($S_1$) |
| $M_{10}$ | Low point of S wave ($S_2$) |
| $M_{11}$ | End of S wave ($S_3$); beginning of ST interval |
| $M_{12}$ | Beginning of T wave ($T_1$) |
| $M_{13}$ | Peak of T wave ($T_2$) |
| $M_{14}$ | End of T wave ($T_3$) |
| $M_{15}$ | Beginning of U wave ($U_1$) |
| $M_{16}$ | Peak of U wave ($U_2$) |
| $M_{17}$ | End of U wave ($U_3$) |
| $M_{18}$ | End of beat |

In the event that there is no Q wave, the break points $M_5/Q_1$, $M_6/Q_2$, and $M_7/Q_3/R_1$ may all coincide.

For example, the sequence $M_2$-$M_4$ identifies the P wave while the sequence $M_5$-$M_{11}$ identifies the QRS complex. It will be appreciated that additional points may be identified, as well, to mark positions that lie between these fiducial points, thereby refining or manipulating the shape of the beat waveform. Each break point may be defined relative to the previous break point. Thus, an x-value would designate the difference in time (width) from one point to the next and a y-value would designate the positive or negative difference in amplitude. Alternatively, each point may be defined by its absolute x-y coordinates representing time and amplitude referenced to the y-and x-axis, respectively.

Either or both of the x and y parameters of a break point may indicate their absolute values, that is their distance from the y-axis or x-axis, respectively, or may indicate their distance along their respective axis from the previous break point. As used herein, the term "x-value" refers to the horizontal distance from one break point to the next and the term "x-coordinate" refers to the distance form the y-axis. Unless otherwise specified, the term y-value refers to the vertical distance from the x-axis.

In order to define a section, it is also necessary to define a path from one break point to the next. The path is identified by an interpolation method i. Some examples of interpolation methods include, but are not limited to, straight line, sinusoidal, square, concave upward, concave downward, notched, among others.

Thus, each break point may be assigned three parameter values x, y, i which together define the location of a break point and the path from the break point to the next break point.

The present invention further provides tools to allow a user to build a beat waveform from a sequence of sections. For example, after logging into a web service, a user may be presented with a series of pages, each illustrating a particular section with a selection of varying shapes and widths (in time). For example, one page may allow a user to select a PQ interval by presenting a one-column, nine row table with the rows showing possible PQ intervals from 120 ms to 200 ms in increments of 10 ms. Another page may allow a user to select the overall RR interval by presenting a one-column, seven-row table with the rows showing possible RR intervals from 0.6 sec. to 1.2 sec. in 0.1 sec. increments. A user may thus make desired selections and construct one or more full heartbeat waveforms. The assembled waveform may then be output as a data file to be loaded into an ECG simulator for research, teaching, testing, and training purposes.

Figure 5:
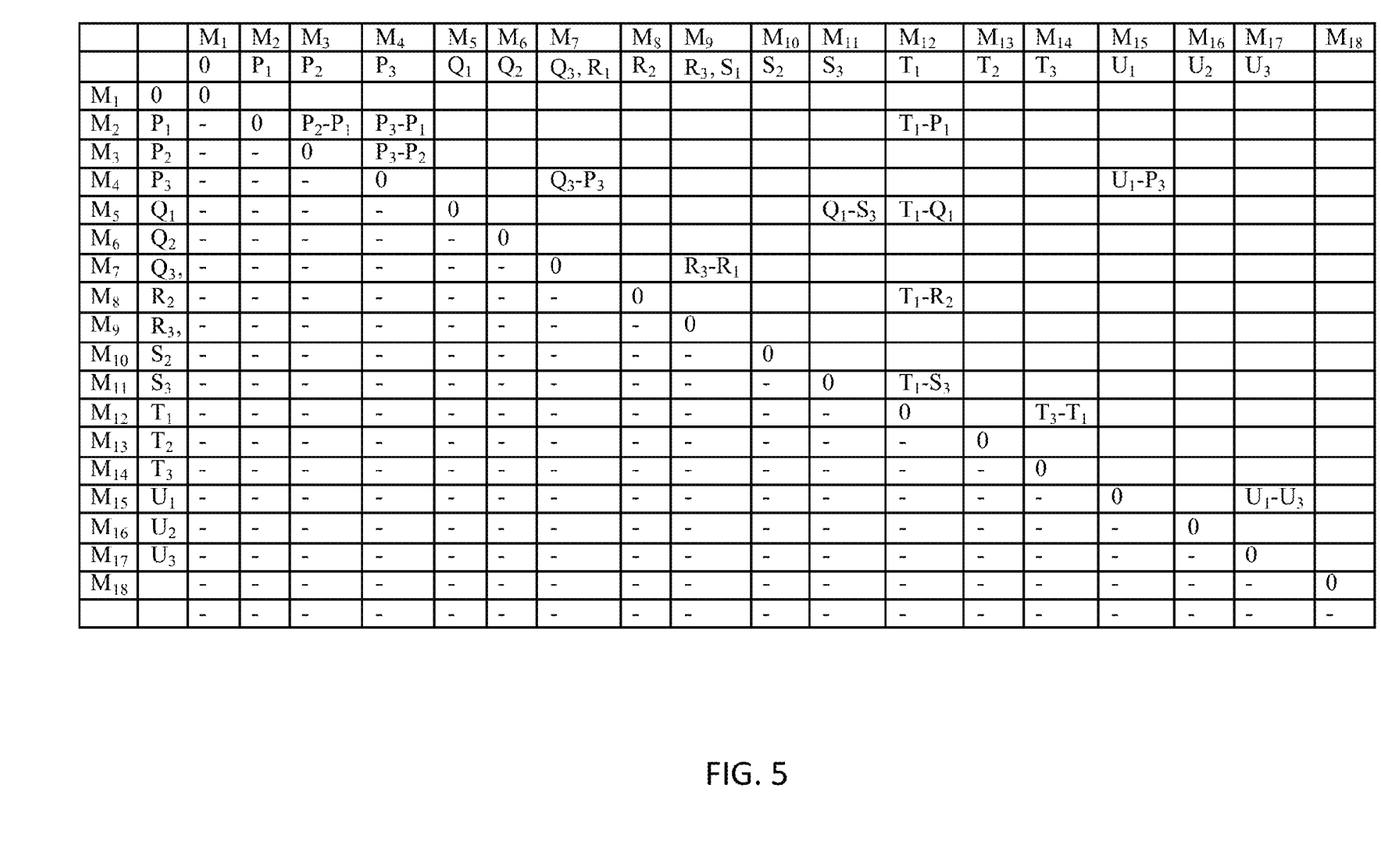
FIG. 5 illustrates a TABLE that may be used to enter information to specify the location of break points when constructing a representation of a heart beat waveform.
Figure 9:
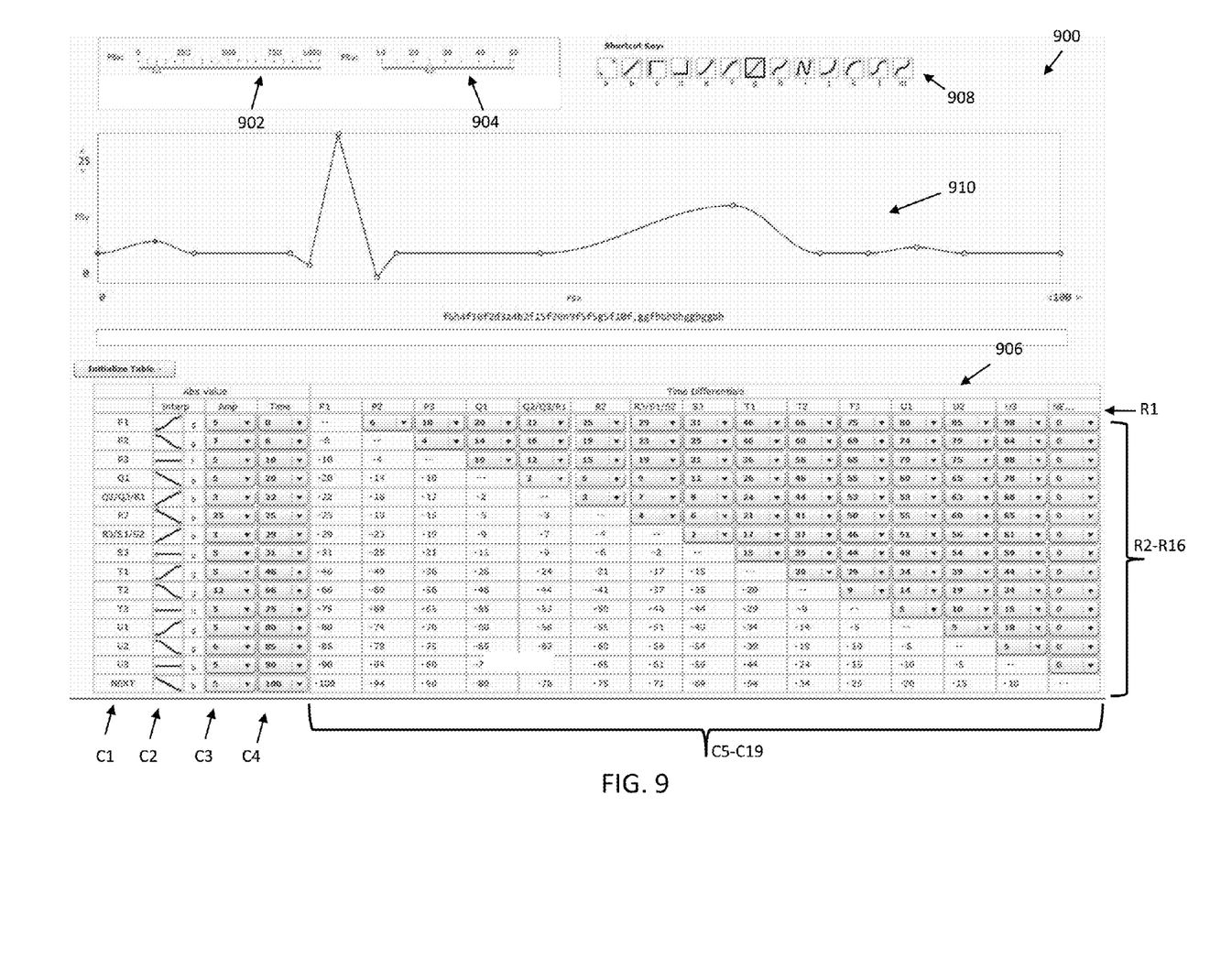
FIG. 9 illustrates a screen shot of a display, including a table with drop-down selections and a representation of an ECG waveform constructed from the selections.

As an alternative to the page-by-page entry method, a user may be presented with a substantially empty table to be filled in with x-values for the break points; that is, time differences from earlier break points. FIG. 5 is an example of a table that may be displayed to the user. The first column and first row identify the break points using the same identification numbers as are used in FIG. 4, $M_1$-$M_{18}$. The second column and second row identify each break point by reference to the wave, interval, or segment in which the break point is located (see TABLE II above). The user may enter a value into each blank cell to designate a time difference between one break point and another. In the table, several cells have been filled in for clarity. For example, to define the total width of the P wave, a value for the time $P_3$-$P_1$ would be entered into the cell at the intersection of column $M_4$ for break point $P_3$ with row $M_2$ for break point $P_1$. Similarly, to define the total width $S_3$-$Q_1$ of the QRS complex, a time value would be entered into the cell at the intersection of column $M_{11}$ for break point $S_3$ with row $M_5$ for break point $Q_3$. The user may fill in as many other cells as desired to specify other time differences. As will be appreciated, the cells at the intersection of break points with themselves have a zero value and the cells that represent negative distances to a previous break point may contain negative values or left blank. In addition, the cells in the row of $M_1$ are unassigned. FIG. 9 illustrates a completed table 906 and the resulting waveform 910 generated by the values entered into the table cells of rows/columns R2-R16/C5-C19.

Figure 6:
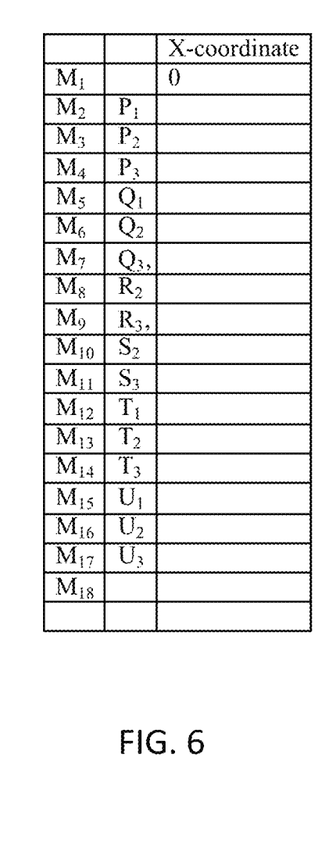
FIG. 6 illustrates another TABLE that may be used to enter information to specify the location of break points when constructing a representation of a heart beat waveform.
Figure 7:
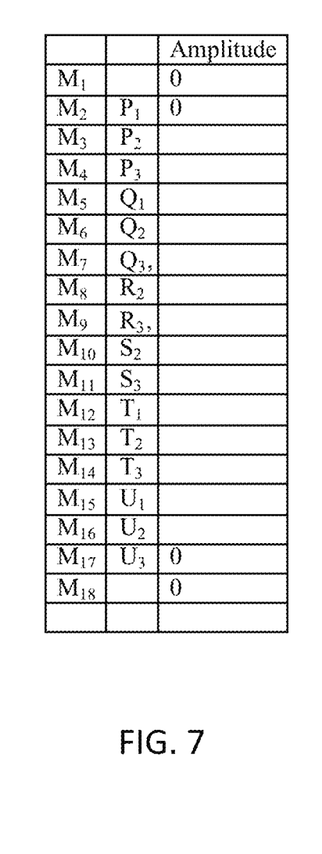
FIG. 7 illustrates another TABLE that may be used to enter information to specify the location of break points when constructing a representation of a heart beat waveform.
Figure 8:
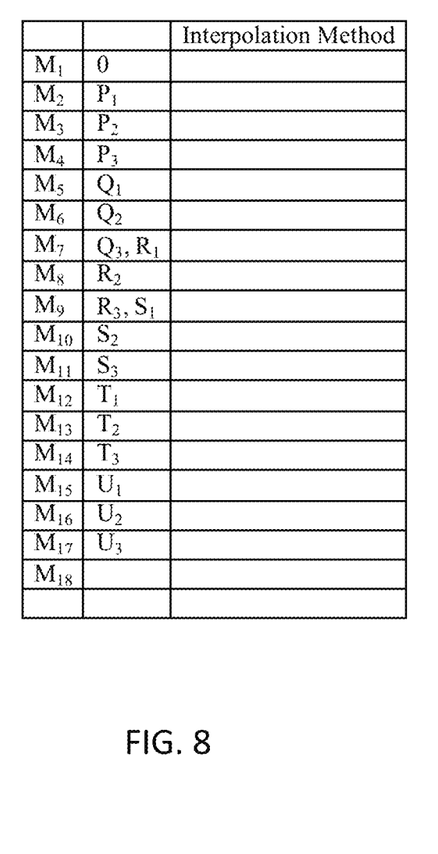
FIG. 8 illustrates still another TABLE that may be used to enter information to specify the location of break points when constructing a representation of a heart beat waveform.

In another embodiment, a simplified table is illustrated in FIG. 6, may be displayed for the user to enter the x-coordinate (the distance from the y-axis) of each break point, $M_1$-$M_{18}$. It will be understood that the break point labels $M_1$-$M_{18}$ and $P_1$-$U_3$ used in the tables of FIGS. 6-8 are the same labels as are used in the tables of FIGS. 4 and 5. After the user has entered coordinates into each cell and has optionally overridden any default coordinates, the user may change any entry by re-entering a coordinate into a cell. However, the user may be prevented from inputting an invalid entry, such as a coordinate that is less than the coordinate of the preceding break point or greater than the coordinate of the next break point.

Another table, shown in FIG. 7, may be displayed for the user to enter the amplitude of each break point, $M_1$-$M_{18}$. Optionally, a default value may be associated with some or all of the break points. For example, as illustrated in FIG. 7, the break points that identify the beginning and end of sections of a beat may default to an isoelectric line while leaving the break points that identify peaks and valleys of waves to be filled in by the user. The user may override any default amplitude value by replacing it with a desired value.

Further, another table, illustrated in FIG. 8, may be displayed for the user to enter the interpolation method for the path from each break point to the next. Again, certain paths may be assigned a default path. For example, the path from $M_4/P_3$ to $M_5/Q_1$ (the PQ segment) may default to a zero-slope straight line. The path from $M_7/R_1$ to $M_8/R_2$ (the first part of the R wave) may default to a straight line whose slope will depend on the amplitude of $M_8/R_2$. And, the path from $M_{12}/T_1$ to $M_{13}/T_2$ (the first part of the T wave) may default to a partial sinusoidal shape whose exact characteristics will depend on the amplitude of the break point $M_{13}/T_2$. As with the amplitude entries, the user may override any default path interpolation method by replacing it with a desired method.

Although in one embodiment, the user may enter coordinates and values in a free-form fashion, in other embodiments the user may be presented with a drop-down list of suggested and valid coordinates or values from which to select.

The tables of FIGS. 7 and 8 are illustrated as separate tables for clarity. In practice, either or both tables may be integrated into the table of FIG. 5 as additional columns and displayed to the user as a single table.

The interactive matrix control/display shown in FIG. 9 has many features that help users learn about their measurement and monitoring tools at the same time they enhance their own skills in using and evaluating these tools. The waveform display 910 is scaled using the FSx control 902 and the FSy control 904. The waveform shape is defined by a shape value directly under the waveform display 910. The text string represents the shape value in an x,y,i format. When using the control/display it is not necessary to know how to interpret the shape value, but it is helpful to understand that the displayed waveform is defined by and may be generated from either the shape value or from the shape data in the matrix. In other words, given the shape value, the system can generate the waveform and populate the matrix with data. Vice versa, given the matrix data the system can generate the waveform and the shape value. The matrix contains more data than the shape value, but all the matrix shape data can be derived from the shape value. To generate the waveform, the system needs x,y, and i data for each breakpoint, 14 in this case. If three independent break points were defined for each of the six fiducial points (PQRSTU), 18 points would be required, but in this case fiducial points Q2/Q3/R1 share one point and R3/S1/S2 share one point. So only fourteen breakpoints are required for eighteen fiducial points. Sixteen break points are identified for the waveform shown in FIG. 4 because Q2 and S2 each have their own break point leaving only Q3/R1 to share one point and R3/S1 to share another.

FIG. 9 illustrates a screen shot of an interactive control/display 900 that may be presented to a user to construct an ECG waveform. Using a touch screen, mouse, or other input device, the user may select a range of values for the x-axis 902 and for the y-axis 904. The lower portion of the display 900 presents a matrix 906 of one variation of the table of FIG. 5 with elements of FIGS. 7 and 8 and other features integrated into it. The first row R1 and first column C1 identify the three break points corresponding to fiducial points for each wave P, Q, R, S, T, and U. Because some break points typically coincide with other break points with no change in x and y coordinates, they are not shown separately. The cells in the second column C2 allow the user to select an interpolation method i, such as from a list or icon display 908. The cells in the third and fourth columns C3, C4 allow the user to select, such as from drop-down lists, the absolute amplitude (along the y-axis) and the absolute time (along the x-axis), respectively, of each break point. The cells at the intersections of the remainder of the rows R2-R16 and columns C4-C18 provide drop-down lists that allow the user to select values that represent the time differential between the break point identified in column C1 and the break point identified in row R1. Cells at the intersection of break points with themselves represent a zero distance and may be left blank or contain symbols such as dashes that are believed to be more useful than zeros. Negative values are shown in the lower half of the matrix. Thus, for each break point, the user may either enter an x-coordinate (the absolute time along the x-axis) in column C2 or enter an x-value (difference from the previous break point) in an appropriate cell in the main body of the matrix 906.

In addition, the user may select an interpolation method from a set of icons 908 to define a path from one break point to the next, and preferably a column C2 may be inserted to identify the iValue selected for each break point.

Displayed between the x, y, and i selections 902, 904, 908 and the matrix 906 is a complete graphical representation of a heart beat waveform from the first break point to the last. Thus, the user is able to see the creation of the ECG waveform progress as entries are input into the cells of the matrix. The user is further able to change any entry in real time and immediately see the effect on the chart. In one embodiment (not shown), the break points displayed in the waveform representation are aligned with their respective columns in the matrix below.

In still another embodiment, the display of the waveform representation may be interactive whereby the user may use an input device to "grab" and move break points to new locations in the x or y directions directly on the chart.

After the user has entered desired information, the heart beat waveform may be assembled digitally and then output as a data file. The data file may be loaded into an ECG simulator to simulate a patient's heart for testing or training purposes.

Figure 10:
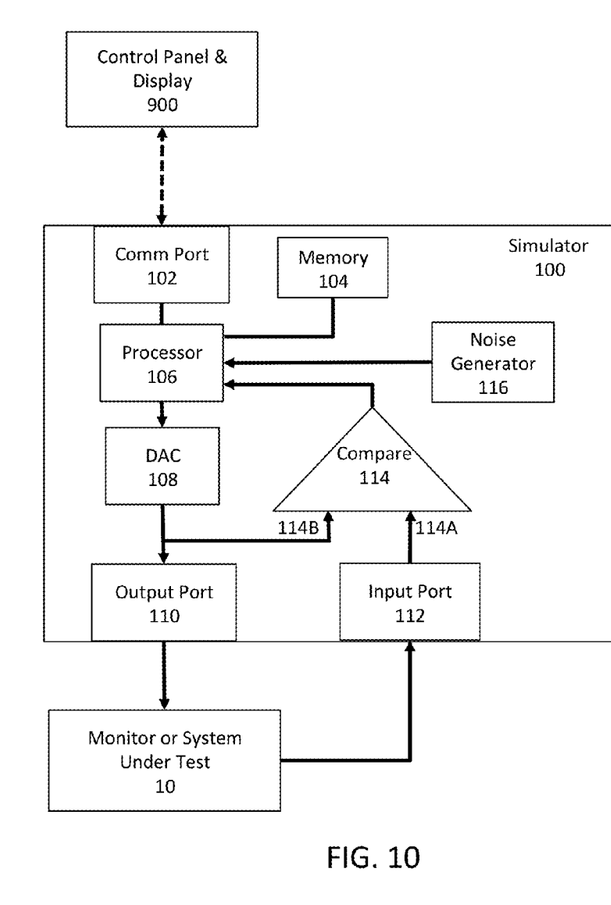
FIG. 10 is a block diagram of an embodiment of a ECG simulator of the present invention.

FIG. 10 is a block diagram of an embodiment of a signal simulator 100 of the present invention. The simulator 100 is coupled to the control and display panel 900 and is configured to output signals to a system under test (SUT) 10, such as an ECG or other biological signal monitor. The panel 900 and simulator 100 may be coupled through a wired connection or, preferably, through a wireless connection, such as WiFi or Bluetooth® enabled. In such a configuration, the panel 900 may thus be used remotely.

The simulator 100 may include a communication (comm) port 102 configured to receive programming signals from the panel 900, a memory 104 configured to store instructions and predetermined values, a processor 106 configured to process the programming and predetermined values according to the instructions stored in the memory, a digital-to-analog converter (DAC) 108 configured to convert the processed values into analog output signals, and an output port 110 configured to make the analog output signals available to the SUT 10. The simulator 100 may also include an input port 112 to receive signals from the SUT 10 and a comparator 114 configured to compare the signals 114A from the SUT 10 against the signals 114B from the DAC 108. A comparison of the signals, such as in graphical form, may then be displayed on the panel 900. Although the input port 112 and the comparator 114 are shown in FIG. 10 as being digital components, they may instead be analog components, in which case the input signals 114B would be received directly from the processor 106 without conversion.

The panel 900 may be part of any appropriate input and display product, such as a computer, tablet computer, or smart phone, to receive programming values from a user, output programming signals to the simulator 100, and receive signals for display from the simulator 100.

The simulator 100 may transmit simulated physiological electrical (biological process) signals to the monitor SUT 10 in place of signals from patient electrodes for the purpose of testing or verifying various functions of the monitor. When the SUT 10 is an ECG monitor, such functions may include those related to variations in heart rate. As noted above, the comparator 114 is configured to compare the signals from the SUT 10 against the signals from the DAC 108 and a comparison of the signals may then be displayed on the panel 900. In this manner, the performance of the SUT 10 may be verified and adjustments may be made as required, such as if the two signals are misaligned.

The simulator 100 may also be programmed to identify when the differential between two break points falls outside of a predetermined range, thus indicating the possibility of an abnormality. For example, when the simulator 100 is coupled to an ECG monitor (SUT 10), it may measure the time between the $T_3$ break point to the next $R_2$ break point. If time is less than about 260 ms, a heart irregularity may be indicated and the simulator 100 may provide an appropriate warning signal to the user.

The raw signal that is received by an ECG monitor is not "pure" in that the electrodes also pick up unrelated electrical activity, circuitry noise, and other artifacts, all collectively referred to herein as noise. An ECG monitor includes circuitry to filter out the noise so that the wave form that is displayed is relatively clean. The simulator 100 may also include a noise generator 116 and be programmed to inject or mix noise into a user-created ECG wave form to more accurately simulate the signals from an actual patient's heart. The mixed signal is transmitted to the monitor or SUT 10 through the output port 110, fed back to the simulator 100 through the input port 112, and compared 114 to the transmitted signal. In this manner, the capability of the monitor or SUT 10 to filter the noise and leave only the useful information may be assessed.

The simulator 100 may provide an additional training benefit by allowing users to generate custom designed ECG waveforms for study, instead of having to find and study actual ECG patient charts that may be unclear, inconsistent, noisy, or contain various artifacts.

The description of the present invention has been presented for purposes of illustration and description, but is not intended to be exhaustive or limited to the invention in the form disclosed. Many modifications and variations will be apparent to those of ordinary skill in the art. The embodiments were chosen and described in order to best explain the principles of the invention, the practical application, and to enable others of ordinary skill in the art to understand the invention for various embodiments with various modifications as are suited to the particular use contemplated.

What is claimed is:

1. A system for generating electrical signals, comprising:
a panel, comprising:
  a first location for displaying and editing shape values, the shape values representing coordinates for a plurality of break points;
  a second location for displaying and editing a shape illustration generated from the shape values; and
  a control module for adjusting the shape values and shape illustration, the control module comprising an input configured to receive from a user the shape values and adjusted shape values, and further configured to output programming signals represented by the shape values and shape illustration; and
a simulator, comprising:
  a communication port configured to receive the programming signals from the input;
  a memory configured to store instructions and predetermined values;
  a processor configured to process the programming signals and predetermined values according to the instructions stored in the memory; and
  an output port configured to make the processed signals available to a system under test (SUT) as electrical signals.

2. The system of claim 1, the simulator further comprising:
an input port configured to receive signals output from the SUT;
a comparator configured to compare the processed signals from the processor with the signals from the SUT; and
output a comparison signal through the communication port for display to a user.

3. The system of claim 2, wherein the comparator is a digital comparator configured to compare digital processed signals from the processor and digital signals from the SUT.

4. The system of claim 2, the simulator further comprising a digital-to-analog converter (DAC) configured to convert the processed signals from the processor into first analog signals, wherein the comparator is an analog comparator configured to compare analog processed signals from the processor and analog signals from the SUT.

5. The system of claim 2, wherein the control module input is further configured to receive second values from the user to correct a misalignment between the signals output from the SUT and the processed signals from the processor.

6. The system of claim 1, wherein the shape values represent coordinates of a plurality of breakpoints and the instructions stored in the memory and processed by the processor include instructions to:
identify when a differential between two break points falls outside of a predetermined range; and
indicate to the user of the presence of a possible abnormality.

7. The system of claim 2, whereby the processor is further configured to:
mix programmed noise from a noise generator with the programming signals; and
indicate to the user how much noise the SUT has removed.

8. A method of generating simulated ECG electrical signals, comprising:
displaying an interactive matrix for user input, the matrix comprising:
  a first row in which a plurality of break points is labeled, the break points identifying the beginning and end of ECG Q, R, S, T, and U waves and a point between the beginning and end of each wave;
  a first column in which the plurality of break points is labeled;
  a second column configured to receive user input of an amplitude value of each break point on a y-axis;
  a third column configured to receive user input of a time value of each break point on an x-axis; and
  a plurality of cells in a remaining portion of the matrix configured to receive user input of a time differential between two adjacent break points;
providing a user with a selection of interpolation methods to define a connection path from one break point to a next break point;
as values for each break point are accepted by the user, displaying the break point on a chart as a portion of an ECG waveform, including the connection path from each break point to the next break point;
converting the entered values into an analog signal simulating an ECG waveform; and
providing the analog signal to an input of an ECG monitor whereby the ECG monitor outputs a graphical display of the simulated ECG waveform.

9. The method of claim 8, further comprising comparing the graphical display of the heart beat waveform output from the ECG monitor with a graphical display of the input to the ECG monitor.

10. The method of claim 8, further comprising indicating for the user when a differential between two break points falls outside a predetermined range.

11. The method of claim 8, further comprising mixing values representing noise into the data file representing the heart beat waveform before providing the data file to the input of the ECG monitor.

12. A system for generating simulated ECG electrical signals, comprising:
an input configured to receive first values, the first values representing coordinates for a plurality of break points of a heart beat wave form, and further configured to output programming signals;
a communication port configured to receive the programming signals from the input;
a memory configured to store instructions and predetermined values;
a processor configured to process the programming signals and predetermined values according to the instructions stored in the memory;
an output port configured to make the processed signals available to an ECG monitor as simulated ECG signals.

13. The system of claim 12, further comprising:
an input port configured to receive signals output from the ECG monitor;
a comparator configured to compare the processed signals from the processor with the signals from the ECG monitor and generate a comparison signal; and
an output configured to output the comparison signal through the communication port for display to the user.

14. The system of claim 13, wherein the comparator is a digital comparator configured to compare digital processed signals from the processor and digital signals from the ECG monitor.

15. The system of claim 13, further comprising a digital-to-analog converter (DAC) configured to convert the processed signals from the processor into first analog signals, wherein the comparator is an analog comparator configured to compare analog processed signals from the processor and analog signals from the ECG monitor.

16. The system of claim 13, wherein the input is further configured to receive second values from the user to correct a misalignment between the signals output from the ECG monitor and the processed signals from the processor.

17. The system of claim 12, wherein the instructions stored in the memory and processed by the processor include instructions to:
identify when a differential between two break points falls outside of a predetermined range; and
indicate to the user of the presence of a possible abnormality.

18. The system of claim 12, whereby the processor is further configured to:
mix programmed noise from a noise generator with the programming signals; and
indicate to the user how much noise the ECG monitor has removed.

19. A method of generating electrical signals, comprising:
providing an interactive control panel;
displaying on the interactive control panel a matrix wherein each cell in the matrix is identified by the intersection of a row and a column;
labeling each row and each column for identifying a break point representing a fiducial point of an electrical signal to be generated;
receiving for each cell contents comprising the time difference between the fiducial points that identify the cell;
receiving for each break point a method to define a connection path from the break point to a next break point;
converting the contents of the matrix cells into an analog signal representing the electrical signal to be generated; and
outputting the analog signal for graphical display of the generated electric signal.

20. The method of claim 19, wherein outputting the analog signal for graphical display comprises providing the analog signal to an input of a system under test (SUT).

21. The method of claim 20, further comprising comparing the graphical display output from the SUT with a graphical display of the input to the SUT.

22. The method of claim 20, further comprising mixing values representing noise into the analog signal before outputting the analog signal to the input of the SUT.

23. The method of claim 19, further comprising indicating for the user when a differential between two break points falls outside a predetermined range.

* * * * *